United States Patent [19]

Blakemore et al.

[11] 4,171,244
[45] Oct. 16, 1979

[54] ENZYME-BOUND-POLYIDOTHYRONINE

[75] Inventors: Judith I. Blakemore, Mill Valley; Richard K. Leute, Sunnyvale; Roberta D. Ernst, Mountain View, all of Calif.

[73] Assignee: Syva Company, Palo Alto, Calif.

[21] Appl. No.: 778,514

[22] Filed: Mar. 17, 1977

Related U.S. Application Data

[60] Division of Ser. No. 644,408, Dec. 29, 1975, Pat. No. 4,043,872, which is a continuation-in-part of Ser. No. 551,566, Feb. 20, 1975, abandoned.

[51] Int. Cl.$^2$ .................. C07G 7/02; G01N 31/14
[52] U.S. Cl. .................................... 435/188; 424/12; 435/7

[58] Field of Search ............... 195/63, 99, 103.5 R, 195/103.5 A; 424/12

[56] References Cited

U.S. PATENT DOCUMENTS

| 3,817,837 | 6/1974 | Rubenstein et al. | 195/68 X |
| 4,040,907 | 8/1977 | Ullman et al. | 195/103.5 R |

*Primary Examiner*—David M. Naff
*Attorney, Agent, or Firm*—Bertram I. Rowland

[57] ABSTRACT

An enzyme-polyiodothyronine conjugate for use in determining polyiodothyronine by immunoassay is prepared containing an enzyme which is reversibly deactivated by polyiodothyronine and is reactivated by an antibody binding to the polyiodothyronine of the conjugate. Preferred enzymes are malate dehydrogenase and triose phosphate isomerase.

13 Claims, No Drawings

ENZYME-BOUND-POLYIDOTHYRONINE

CROSS-REFERENCE TO RELATED APPLICATION

This application is division of application Ser. No. 644,408, filed Dec. 29, 1975, now U.S. Pat. No. 4,043,872, which is a continuation-in-part of application Ser. No. 551,566, filed Feb. 20, 1975, now abandoned.

BACKGROUND OF THE INVENTION

1. Field of the Invention

The concentration of thyroxine in the bloodstream is within relatively narrow limits critical to the proper functioning of the body. The concentration of thyroxine is extremely small and can only be detected in very sensitive techniques.

The triiodothyronines (T-3) are also an important factor in the healthy functioning of the body. The T-3's differ from thyroxine (T-4) in lacking the 5- or 5'-iodo. It is believed that the T-3's significantly affect the overall metabolic effects of thyroid hormones.

One technique which is employed for the determination of thyroid hormones is radioimmunoassay. While this technique has many variations, it employs the combination of an antibody for the thyroid hormone and radioactive or hot thyroid hormone with blood serum and a separation of the bound hormone from unbound hormone. The amount of hot hormone, which is bound to antibody or remains free, will be a function of the amount of hormone in the serum. By determining the radioactivity of the solution freed from antibody, one can calculate the amount of hormone based on standards employing known amounts of hormone.

The use of radioimmunoassay requires a separation step which introduces errors and can be time-consuming. In addition, one must work with radioactive materials which decay and, therefore, have a limited shelflife. Also, working with radioactive materials is generally undesirable because of health hazards. There is a continuing need for a simple technique which minimizes the manipulative steps, while providing a high degree of sensitivity.

2. Brief Description of the Prior Art

U.S. Pat. No. 3,817,837 describes an enzyme assay which is found to be generically useful for a wide variety of ligands.

SUMMARY OF THE INVENTION

A homogeneous enzyme immunoassay technique is employed for the determination of thyroid hormones. The enzyme reagent employed in the immunoassay is an enzyme-bound-polyiodothyronine (EBP), employing an enzyme which upon conjugation to a polyiodothyronine is more than about 50 percent deactivated and upon binding of receptor for the polyiodothyronine, is partially or completely reactivated. Thus, the conjugated enzyme which is employed has a low turnover rate, which is substantially increased in the presence of receptor, for example, antibody for polyiodothyronine.

The assay is carried out by combining in an aqueous buffered medium a serum sample to be measured, the appropriate receptor, EBP, and the enzyme substrates, and determining the rate of the enzyme catalyzed reaction. One or more incubation periods may optionally be included between reagent additions. By preparing standards having known amounts of T-3, reverse T-3 or T-4, a calibration curve can be prepared to which unknown samples may be related.

The EPB compositions have on the average at least one polyiodothyronine bonded to the enzyme through an aliphatic carbon atom or non-oxo-carbonyl group (including nitrogen and thio-analogs thereof) forming an amide (amidine or thioamide respectively) and/or ester.

DESCRIPTION OF THE SPECIFIC EMBODIMENTS

A method and compositions are provided for determining polyiodothyronines (T-3 and T-4) at concentrations as low as $10^{-7}$ M or lower, which is a homogeneous enzyme immunoassay. By analogy to the invention described in U.S. Pat. No. 3,817,837, T-3 and T-4 are the ligands, enzyme-bound-ligand is enzyme-bound-T-3 or -T-4, and antiligand is antibody for T-3 or T-4. Particularly, the enzymes are malate dehydrogenase or triose isomerase.

The homogeneous enzyme immunoassay of this invention employs as reagents enzyme-bound-polyiodothyronine, particularly T-3 and T-4, receptor for polyiodothyronine, particularly antibody, e.g., anti-T-3 and anti-T-4, substrates for the enzyme and an aqueous, normally alkaline, buffer medium, usually having one or more additives for enhancing enzyme stability, for measuring the product of the enzyme reaction, or the like. The order of the addition of the reagents to the aqueous assay medium is not critical, although particular protocols will be preferred. In addition, incubation may be desirable after the addition of particular reagents.

After all the reagents have been added, the rate of reaction for the enzyme will be followed, normally spectrophotometrically. By comparing the result obtained with the unknown to results obtained employing known amounts of the polyiodothyronine, the amount of polyiodothyronine in the unknown can be determined.

The order of description of this invention will be a description of the reagents first, followed by a description of the assay.

REAGENTS

Enzyme-Bound-Polyiodothyronine

In preparing the enzyme-bound-polyiodothyronine, one may use the polyiodothyronine directly, activating the carboxyl group to be bound to available groups on the enzyme, e.g., lysines and tyrosines, or preferably, provide an extended chain from the available functionalities such as the amino group or the carboxy group, particularly the amino group. The phenolic hydroxyl group will not be used as a site for conjugation.

The enzymes which find use are those which are substantially reversibly deactivated upon conjugation of a polyiodothyronine, so that upon binding to an antibody for polyiodothyronine, substantial activity is recovered. Only a select group of enzymes are found to have this activity, particularly malate dehydrogenase, more particularly mitochrondrial, preferably pig heart mitochrondrial malate dehydrogenase (MDH) and triose phosphate isomerase, particularly rabbit muscle triose isomerase (TIM). Usually, the polyiodothyronine will be bound to the enzyme by a linking group which is linked to the amino group of the polyiodothyronine, with the carboxy group esterified, particularly with a lower alkyl group, usually of from one to three carbon atoms. Conveniently, the polyiodothyronine may be bonded through a functional group which has two non-oxo-carbonyl functionalities. (For the purposes of this invention, non-oxo-carbonyl shall mean the oxygen containing carboxy $$-\overset{O}{\underset{\|}{C}}-OH$$

the nitrogen containing imidic group $$-\overset{NH}{\underset{\|}{C}}-OH$$

the sulfur containing thionocarboxy $$-\overset{S}{\underset{\|}{C}}-OH$$

and the derivatives thereof, e.g., amides, esters and anhydrides.)

The number of polyiodothyronines conjugated to the enzyme on the average will be at least one and not more than about ten per enzyme, usually one to eight and more usually two to six. The polyiodothyronines may be joined to available sites, e.g., amino or hydroxy to form amides and esters, by any convenient linking group from the amino group or carboxy group, particularly the amino group, of the polyiodothyronine. Since the amino group will have to be protected during conjugation, when the carboxyl group is involved in the conjugation, for the most part linking groups will be attached to the amino site. Conveniently, the ester of the polyiodothyronine will be employed and a group having a non-oxo-carbonyl functionality (see the above definition) will be employed for conjugation to amino and hydroxyl groups of the enzyme.

A bond or linking group may join the polyiodothyronine to the enzyme. The particular linking group has been found not to be critical to this invention, although certain classes of linking groups are preferred. The number of atoms in the linking group other than hydrogen will generally be not more than 20, usually not more than 16, and may have from 0 to 7, usually 1 to 6 heteroatoms, particularly chalcogen (O and S), normally bonded solely to carbon, and nitrogen, being bonded solely to carbon and hydrogen and being neutral when bonded to hydrogen e.g. amido.

The particular enzyme which is employed is one which is reversibly deactivated by a polyiodothyronine, so that in the absence of receptor for polyiodothyronine, the enzyme has less than about 50 percent, usually less than about 35 percent, and more usually less than about 25 percent of the original enzyme activity present prior to conjugation, retaining at least 0.5 usually at least 1 percent of the original enzyme activity present prior to conjugation. Upon introducing an excess of receptor for polyiodothyronine to the enzyme conjugate, the enzymatic activity will increase by at least 50 percent, more usually at least 100 percent, and frequently by 200 percent or more. The amount of increase in activity will depend to a substantial degree on the original decrease in activity upon conjugation. Other enzymes, particularly dehydrogenases, which are found to be inhibited by thyroxine are reported in Wolff and Wolff, Biochimica et Biophysica Acta, 26, 387 (1957). These enzymes include glutamic dehydrogenase, lactate dehydrogenase, yeast alcohol dehydrogenase, yeast glucose-6-phosphate dehydrogenase and glyceraldehyde-3-phosphate dehydrogenase.

Generically, the EBP will have the following formula:

$$ENZ-\left(\underset{(NHW)_x}{\overset{}{W^1OCCHCH_2Z}}\right)_m$$

wherein:

ENZ is an enzyme which is reversibly inhibited by a polyiodothyronine, particularly T-3 and/or T-4, so that the enzyme is activated when the polyiodothyronine is bound by receptor e.g. antibody; the enzyme will generally be a dehydrogenase or triose phosphate isomerase x is 0 or 1

Z is $$HO-\underset{G^1}{\overset{I}{\bigcirc}}-O-\left(\underset{G}{\overset{I}{\bigcirc}}\right)_{m^1}-$$

wherein:

$m^1$ is 0 or 1;

G and $G^1$ are hydrogen or iodo, with the proviso that $G^1$ is iodo when $m^1$ is 0 and that there are at least 3 iodos when $m^1$ is 1;

one of W and $W^1$ is a linking group, preferably aliphatic, having from 0 to 1 site of ethylenic unsaturation, of from 1 to 20 atoms other than hydrogen, which are carbon, chalcogen, and nitrogen, chalcogen being bonded solely to carbon as oxy or oxo (including thio analogs), particularly non-oxo carbonyl, and nitrogen being bonded solely to carbon and hydrogen and being neutral when bonded to hydrogen e.g. amido; the number of heteroatoms usually being in the range of 1 to 8, more usually in the range of 2 to 7, and preferably 2 to 4; there normally being not more than 5, usually not more than 4, and preferably 2 to 3 functionalities in the linking group chain e.g. tert.-amino, oxy, amido, etc., with the proviso that $W^1$ may be a bond, particularly when x is 0;

when other than a linking group, W is hydrogen and $W^1$ is hydroxyl or alkoxyl of from 1 to 3 carbon atoms, particularly methyl; and m is on the average at least 1 and not more than 10, usually 1 to 8, more usually 2 to 6.

The EBP employed in this invention will for the most part have the following formula $$ENZ-((\overset{X}{\underset{\|}{C}}-A)_a-\overset{Y}{\underset{\|}{C}}NH-\overset{CO_2D}{\underset{|}{CHCH_2Z}})_n$$

wherein:

ENZ is an enzyme which is reversibly inhibited by a polyiodothyronine, particularly T-3 and T-4, so that the enzyme is activated when the polyiodothyronine is bound by receptor; the enzyme will usually be a dehydrogenase, particularly malate dehydrogenase, or triose phosphate isomerase.

n is on the average at least one, and not more than 10, usually 1 to 8, more usually 2 to 6;

a is 0 or 1, usually 1;

X and Y are the same or different and are chalcogen (O or S) or imino (=NH), normally Y will not be imino;

D is hydrogen or an alkyl group of from 1 to 6 carbon atoms; usually 1 to 3 carbon atoms, and preferably 1 carbon atom;

Z is 3,3',5-, 3,5,3'-triiodo- or 3,3',5,5'-tetraiodo-4-(hydroxyphenoxy-1')-phenyl-1 or 3,5-diiodo-4-hydroxyphenoxy; and A is a bond or an organic divalent group of at least one carbon atom, usually at least two carbon atoms, and usually not more than 12 carbon atoms, more usually not more than 10 carbon atoms having from 0 to 12, usually 1 to 10, more usually 2 to 9, and preferably 3 to 7 atoms in the chain (with cyclic groups the greater number of annular atoms will be included) between the non-oxo-carbonyl groups and having from 0 to 4, usually 0 or 1 to 3, more usually 1 to 2 heteroatoms in the chain, which may be chalcogen (O or S) (as oxy, thio or sulfonyl) or nitrogen (tertiary amino or amido); the total number of heteroatoms will be from 0 to 6, generally 0 to 5, usually 0 or 1 to 4, more usually 1 to 3, which will be chalcogen (O or S) (as non-oxo-carbonyl, non-oxo-thiocarbonyl, oxy, thio or sulfonyl) or nitrogen (imino, tertiary amino or amido); there usually being two carbon atoms between heteroatoms in the chain.

A may be hydrocarbylene (aliphatic, alicyclic, aromatic or combinations thereof) or non-hydrocarbylene (substituted aliphatic, alicyclic, aromatic, heterocyclic or combinations thereof), generally having from 0 to 1 cyclic group in the chain, normally of from 5 to 6 annular members having from 0 to 2 heteroannular members, usually 0 to 1 heteroannular member, the cyclic group will usually have substituents separated by from 2 to 4, usually 3 to 4 annular members; normally the hydrocarbylene will have as its only aliphatic unsaturation from 0 to 1 ethylenic groups, and is preferably saturated, particularly preferred is alkylene having from 0 to 1 carboxamido, imino, or oxy group in the chain. When A is carbocyclic aromatic, A will usually have 6 to 10, more usually 6 to 8 carbon atoms.

The total number of functional groups in the chain (oxy, amino, amido and sulfur and nitrogen analogs thereof) will generally be from 0 to 4, usually 0 to 3, and more usually 0 or 1 to 2.

Included within the compound genus are ENZ-bound-T-3 or -T-4 compositions which have a di-non-oxo-carbonyl link having an aliphatic chain which is uninterrupted by heteroatoms or interrupted by from about 1 to 2 heteroatoms, chalcogen and nitrogen. These compounds will for the most part have the following formula:

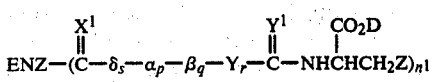

ENZ, D and Z have been defined previously;

$n^1$ has the same limits as n, but is on the average, 1 to 10, preferably 1 to 8, and more preferred 2 to 6;

$X^1$ and $Y^1$ have the same limits as X and Y respectively, with $X^1$ normally being chalcogen, and $Y^1$ preferably being oxygen;

p, q and r are each 0 to 1, with the total of p, q and r preferably equal to at least one (p+q+r≧1);

s is 0 to 2, usually 0 to 1;

α and γ are hydrocarbon groups of from 1 to 8, usually 1 to 6 carbon atoms, more usually of from 1 to 3 carbon atoms, having a total of from 1 to 12 carbon atoms, usually a total of from 2 to 10 carbon atoms, preferably a total of from 2 to 8 carbon atoms, and more preferred a total of from 2 to 6 carbon atoms; where p or r is 0, α or γ is preferably of from 1 to 8 carbon atoms, more preferably of from 1 to 6 carbon atoms; α and γ may be aliphatic, alicyclic, aromatic or heterocyclic and together with 62 and δ come within the definitions of A; preferably α and γ are saturated aliphatic, particularly, unbranched, e.g., methylene or polymethylene or aromatic, particularly monocyclic, where only one of α and γ are aromatic;

β is oxy (—O—), thio (—S—), sulfonyl (—SO₂—) or amino

where T is alkyl of from 1 to 6 carbon atoms, usually 1 to 3 carbon atoms or hydrogen; when β is bonded to non-oxo-carbonyl, (p is 0) normally β will be amino or alkylamino; and δ is

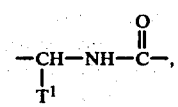

wherein $T^1$ is hydrogen or lower alkyl of from 1 to 3 carbon atoms.

In a preferred subgenus, the polyiodothyronine may be combined with a dibasic dicarboxylic acid to form an amic acid (the monoamid of a dibasic acid). The dibasic acid will normally be of from 2 to 8 carbon atoms, usually 2 to 6 carbon atoms, have from 0 to 1 site of ethylenic unsaturation in the chain, and have from 0 to 1 atoms of atomic number 7 to 8 (nitrogen or oxygen), any nitrogen or oxygen being bonded solely to carbon, i.e. tertiary amino or ether. Preferred dibasic acids form cyclic anhydrides of from 5 to 7, particularly 5 to 6 annular members. In order to insure that the carboxyl group of the dibasic acid conjugated to the thyronine is the one that reacts with the ENZ, the original carboxyl group of the thyronine will normally be esterified with an alkyl group of from 1 to 3 carbon atoms, preferably 1 carbon atom (methyl).

The modified polyiodothyronine or its analog which is employed for conjugation with ENZ will for the most part have the following formula:

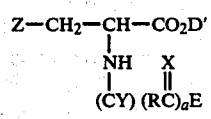

wherein:

X, Y, Z and a are as defined previously;

D' is hydrogen or alkyl or from 1 to 3 carbon atoms, preferably one carbon atom;

R has the same definition as A, but is preferably an aliphatic divalent group having from 0 to 1 site of ethylenic unsaturation and from 0 to 1 heteroatom of atomic number 7 to 8, the heteroatoms being completely substituted by carbon atoms, and is of from 1 to 6 carbon atoms; and E is hydroxyl, or may be taken together with a terminal nitrogen of R to form a double bond, e.g., isocyanate or isothicyanate.

Another convenient series of compounds has a carbocyclic or heterocyclic ring of from 5 to 6 annular members in the chain, the heterocyclic ring having from 1 to 2, usually one heteroannular member, which is O, S or N. Preferably, these compounds have an isocyanate or isothiocyanate bonded directly or indirectly to an annular member, particularly where the ring is aromatic. For the most part these compounds will have the following formula:

$$X^2=C=NArCNHCHCH_2Z$$
with $Y^2$ and $CO_2D$ substituents wherein:

D and Z have been defined previously;

$X^2$ and $Y^2$ are chalcogen (O or S), preferably $X^2$ is S;

Ar is arylene or aralkylene, including carbocyclic and heterocyclic of from 5 to 6 annular members, having from 1 to 2, preferably 1, heteroannular members, which are O, N and S and is of from 4 to 10 carbon atoms, usually 4 to 8 carbon atoms and when heterocyclic, preferably 4 to 6 carbon atoms, and when carbocyclic, preferably 6 to 8 carbon atoms.

The ENZ conjugate of the above series of compounds will have the formula:

$$ENZ-(C-NHArCNHCHCH_2Z)_{n1}$$
with $X^2$, $Y^2$, $CO_2D$ substituents wherein all the symbols have been defined previously.

The polyiodothyronine analog will be employed in an active or activated form, so as to be capable of reacting with available non-oxo-carbonyl reactive groups of ENZ, e.g. amino and hydroxyl.

For the carboxy, a mixed anhydride, a N-hydroxy succinimide, p-nitrophenyl, phenylthio, etc., ester derivative or a carbodiimide coupling reagent is conveniently employed, while imidate esters and isothiocyanates are employed directly for conjugation with ENZ. The reaction is carried out at moderate temperatures generally in the range of about $-5°$ to $30°$ C. in a mixed aqueous buffered medium, usally at a mildly alkaline pH, generally in the range of about 7 to 10. A co-solvent may be employed, e.g. hexamethylphosphoramide. The co-solvent when employed will generally be used in amounts of about 10 to 40 percent, preferably from about 20 to 30 volume percent.

The mole ratio of T-3 or T-4 analog to ENZ molecules will generally vary from about 1:1 to 20:1, more usually from about 3:1 to 10:1.

The T-3 or T-4 analog may be added incrementally or in bulk and the reaction time will generally vary from about 1 minute to about 48 hours. At the end of this time, the reaction mixture may be worked up according to conventional techniques. Preferably, the mixture is chromatographed, so as to separate any unreacted analog from the ENZ-bound-T-3 or T-4. A convenient chromatographic material is Sephadex. The fractions may be isolated, their enzyme activity determined, and those fractions having enzyme activity pooled.

Rather than an analog formed by combining the polyiodothyronine with a di-non-oxo-compound, desamino-T-3 or T-4 may be conjugated to ENZ. With the polyiodothyronine, the amino group must be protected when conjugating ENZ with the amino acid, while with the desaminopolyiodothyronine, no protective group is required and the carboxy group may be activated in the same manner as the other carboxy groups.

The desaminopolyiodothyronine or its monocyclic analog will come within the following formula:

$$HO_2CCH_2(CH_2)_tZ$$

where

Z has been defined previously, and t is 0 or 1;

while the ENZ conjugate of these compounds will have the following formula $$ENZ-(COCH_2(CH_2)_tZ)_{n1}$$

wherein all the symbols have been defined previously.

The ENZ-bound-T-3 or -T-4 will normally be at least about 50 percent deactivated in comparison to the enzyme activity present prior to conjugation, usually at least about 65 percent deactivated and not more than about 99.5 percent deactivated. Desirably, the enzyme would be almost completely deactivated and its activity substantially completely restored upon addition of excess anti-T-3 or -T-4. However, it is found that the conjugated enzyme is activated by binding to receptor to from about 5 to 60% of the original activity of the unconjugated enzyme, usually from 10 to 50% of the original activity of the unconjugated enzyme. The primary concern is the spread in measured units between ENZ-bound-T-3 or T-4 in the absence of antibody and in the presence of excess antibody. By excess is intended sufficient antibody to bind substantially all the available T-3 or T-4.

The enzyme is conveniently mitochondrial pig heart malate dehydrogenase or rabbit muscle triose phosphate isomerase.

Anti-T-3 or T-4

The appropriate antibodies are produced by the injection of a T-3 or T-4-bound-antigen into a vertebrate, usually a domestic animal, e.g. sheep, rabbit or goat. Since the antigen is normally a polypeptide or protein, normally of from about 5,000 to 10 million molecular weight, the conjugated antigen will be formed by the combination of a T-3 or T-4 analog and the antigenic polypeptide or protein. Either the same or different analog may be used from the analog employed for the conjugation with ENZ. Besides the analogs employed for preparing the conjugate, other anlogs may be employed. In addition, thyroglobulin may be employed for the production of antibodies.

Depending upon the particular analog which is employed, various techniques which have been described in the literature may be used for the preparation of the anti-gens. The antigens will have at least one analog molecule and, preferably, from about 1 per 2,000 molecular weight of the antigen to about 1 per 50,000 molecular weight of the antigen. The ratio of T-3 or T-4 analogs to molecular weight will increase with the decreasing molecular weight of the antigen.

The injection of the antigen into the animal will follow conventional techniques, although it may be preferable to use complete Freund's adjuvant with the booster injection.

A wide variety of proteins may be employed as antigens, such as albumins, globulins, keyhole limpet hemocyanin, and the like.

Buffer

The buffers employed may be widely varied and include phosphate, carbonate, glycinate, Tris, and the like. Phosphate should not be employed in high concentrations, >0.1 M. One buffer may be preferred over another buffer, with glycinate or triethanolamine being the preferred buffers.

Other Additives

Depending upon the course of reaction, the substrates for MDH will be malate and NAD or oxaloacetate and NADH. For triose phosphate isomerase (TIM) the enzymatic reaction of the enzyme is coupled with a second enzyme to allow for spectrophotometric determination. Therefore, included in the assay medium is the substrate for TIM, glyceraldehyde phosphate, NADH, and alpha-glycerophosphate dehydrogenase. The latter enzyme and NADH are used in substantial excess, so as not to be rate limiting.

Advantageously, a small amount of ethylenediaminetetraacetic acid is included to reduce bacterial growth and sequester heavy metals. A protein and glycerol may also be included in the assay medium to enhance enzyme stability. Additional stabliizers such as dithioerythritol or other antioxidants may also be included. Also, small amounts of sodium azide may be added as a preservative.

ASSAY

Reagent Solutions

The buffer solution employed will normally be at a concentration to provide in the assay medium a concentration of from about 0.001 to 0.5 M, usually from about 0.01 to 0.2 M, and preferably from 0.05 to 0.15 M. The protein which is included, which is conveniently an albumin, such as rabbit serum albumin and/or gelatin, will generally be present in about 0.005 to 0.5 weight percent in the final assay mixture, more usually from about 0.01 to 0.2 weight percent. Glycerol may be present in from 0.1 to 5, usually 0.4 to 4 weight percent. The pH of the solution will generally be from about 6.0 to 10.5, usually from about 7 to 10.5, and more usually about 8 to 10, and preferably from 8.5 to 10.5 when NAD and malate or NADH and oxaloacetate are employed, and preferably from 7 to 9 when glyceraldehyde phosphate is employed.

In the assay medium, the concentration of ENZ may be varied widely, but will generally be in the range of about $10^{-5}$ to $10^{-12}$ M, more usually from about $10^{-7}$ to $10^{-11}$ M. The antibody concentration will be based on a ratio of antibody binding sites to the concentration of polyiodothyronines bound to the ENZ. Generally, the ratio of binding sites to T-3 or T-4 as ENZ-bound-T-3 or -T-4 will be at least 0.5 and not greater than 1000, more usually being from about 1 to 100, and most usually from about 1 to 25. Usually sufficient antibody is added to recover from 25 to 75, preferably 25 to 50% of the recoverable enzyme activity.

Increased amounts of antibody will be required with decreasing binding constants. The specific amount of antibody employed in a specific assay will normally be determined empirically.

Other minor additives which may be added include ethylenediaminetetraacetic acid, which may be present in from about 0.001 to 0.1 weight percent, sodium azide which may be present in from about $10^{-5}$ to $10^{-3}$ M and a surfactant such as Triton X-100 which may be present in from about 0.0001 to 0.03 weight percent.

When employing MDH, depending on the direction of the reaction, either malate and NAD or oxaloacetate and NADH will be employed, the former being preferred. The concentration of these materials directly affects the assay sensitivity and must be determined empirically so as to optimize the difference in the rate of the reaction in the presence and in the absence of added antibody. The concentration of malate or oxaloacetate will generally be from about 0.01 to 0.5 M, more usually from about 0.05 to 0.3 M. The concentration of NAD or NADH will generally range from about 0.001 M to 0.05 M, more usually from about 0.005 M to about 0.2 M. Normally, the concentrations of the enzyme, antibody, and substrates are chosen to optimize the sensitivity of the assay.

When TIM is employed, the glyceraldehyde phosphate will generally be at a concentration in the range from about $10^{-1}$ to $10^{-4}$ M, alpha-glycerophosphate dehydrogenase will generally be present in amounts of $10^{-5}$ to $10^{-9}$ M, while NADH concentrations will generally be from about $10^{-2}$ to $10^{-4}$ M.

The various reagents can be conveniently added as aqueous solutions. Normally, a large proportion of the total assay sample will be the buffer solution.

Assay Steps

The order of combination of the various reagents is not critical, although some orders are preferred and in some instances, one order will be preferred over another. Incubation may be employed after the addition of any particular reagent or after all the reagents have been combined. Usually, the assay mixture will not be incubated in the presence of the enzyme substrates for more than 10 minutes prior to beginning the rate measurement.

All of the reagents may be combined simultaneously. Alternatively, the sample, e.g. serum, buffer and antibody may be combined, optionally followed by incubation. In most instances, antibody and the conjugated ENZ will not be combined prior to addition of the sample. However, when monovalent antibody is employed so as to avoid precipitin formation, it may for certain applications be desirable to store a mixture of the antibody and enzyme.

Depending on the order of addition, the events that occur will be different. If the sample and antibody are combined, the polyiodothyronine will bind to the antibody and reduce the number of available sites for binding to the ENZ-bound-T-3 or -T-4. The concentration of available binding sites will therefore be a function of the amount of T-3 or T-4 in the sample. When the ENZ-bound-T-3 or T-4 is added, the amount of antibody that binds to the conjugated T-3 or T-4 will be a function of the T-3 or T-4 in the sample. This procedure is less sensitive to differences in binding constants between T-3 or T-4 and ENZ-bound-T-3 or -T-4 respectively.

Alternatively, one can combine the sample, the appropriate antibody and the conjugated ENZ and allow the free T-3 or T-4 to compete with the T-3 or T-4 conjugated to ENZ for available binding sites.

Optionally, the assay mixture may be incubated after each addition of a reagent, either before or after addition of the enzyme substrates or other reagents. Incubation may vary from 2 minutes to 1 hour, and will generally be at temperatures in the range of about 15° to 40° C., usually about 25° (ambient) to 37° C.

After addition of the mixture to the substrates for the enzyme, the mixture may be incubated for up to about 10 minutes prior to an initial reading which may be done employing either a flow cell or a cuvette. The rate is determined at a temperature in the range of about 20° to 40° C., more usually from about 25° to 37° C. Generally, readings will be of a duration of from about 0.1 to 45 minutes, usually 0.5 to 2 minutes, when a flow cell is used, and 5 to 45 minutes when a cuvette is used. Measurement periods of 5–20 minutes are useful for certain automated instruments.

By employing standards having known amounts of $T_3$ or $T_4$ in serum, one can establish a calibration curve which can be used for the determination of the amount of $T_3$ or $T_4$ present in an unknown.

While spectrophotometric techniques are most convenient for following the course of the enzyme reaction, namely following the absorption spectrum, other techniques may also be employed such as fluorimetry, titrimetric, etc.

The following examples are offered by way of illustration and not by way of limitation.

EXPERIMENTAL (All temperatures not otherwise indicated are in Centigrade. All percents not otherwise indicated are by weight.)

EXAMPLE I

N-Methyl, N-carboxymethylglycyl Thyroxine Methyl Ester ($T_4$-MEMIDA)

Into a 25 ml flask equipped with stirrer and septum stopper was charged 1.054 g ($1.27 \times 10^{-3}$ mole) of the methyl ester of thyroxine hydrochloride. The thyroxine ester hydrochloride was dissolved under an argon blanket in 8 ml of dimethyl formamide (DMF) to which was added 10 ml of dry tetrahydrofuran (THF), followed by the addition of 253 μl of dry triethylamine.

After stirring the mixture for 15 minutes, 0.279 g ($2.16 \times 10^{-3}$ mole) of N-methyl iminodiacetic acid anhydride in 2.5 ml of dry THF was added in one addition. The reaction appeared to occur instantaneously. Volatiles were removed in vacuo on a rotary evaporator to leave a foamy solid which was dissolved in 25 ml THF and the THF solution extracted with a combination of 30 ml of deionized water and 50 ml of ethyl acetate. After extraction and separation, the aqueous layer was extracted three times with 25 ml portions of ethyl acetate. The organic layers were combined, extracted once with 50 ml of saturated NaCl solution and then dried with anhydrous magnesium sulfate. After suction filtration of the organic layer, the solvent was removed on a rotary evaporator to yield a white solid which was dissolved in 30 ml of THF. To the THF was added 35 ml of chloroform, the solution heated to reflux, and n-heptane added slowly. The volume of the solution was reduced until a definite cloud persisted. The solution was allowed to cool at room temperature, followed by cooling in a freezer, to yield a white fluffy product, which was washed with 1-hexane, and dried in vacuo over phosphorus pentoxide to yield 1.26 g (75%) of a fluffy white product.

EXAMPLE II

Conjugation of $T_4$-MEMIDA to Bovine Serum Albumin (BSA)

To a reaction vessel equipped with stirrer and septumed glass stopper was charged 0.10 g ($1.09 \times 10^{-4}$ mole) of $T_4$-MEMIDA and 0.013 g ($1.1 \times 10^{-4}$ mole) of N-hydroxysuccinimide. To the reaction vessel under an argon blanket was added one ml of dry THF followed by the addition of 15 μl of dry triethylamine. After cooling the mixture in an ice bath to 0°, 0.024 g ($1.25 \times 10^{-4}$ mole) of 1-ethyl-3-(3'-dimethylaminopropyl) carbodiimide hydrochloride (ECDI) was added as a powder. The mixture was stirred for 2 hours at 0° followed by 12 hours at 4°. A solution was prepared of 0.100 g ($1.55 \times 10^{-6}$ mole) of BSA in 3.0 ml of sodium bicarbonate-carbonate buffer, pH 9.4, and the pH readjusted to 9.5 with 6 N sodium hydroxide. The BSA solution was cooled to 0° and the previously prepared $T_4$-MEMIDA ester solution added dropwise at a rate of 50 μl per minute with vigorous stirring. The mixture was then stirred for 1.3 hours at 0°, followed by stirring gently for 2 days at 4°.

To the solution was then added dropwise a 3 M hydroxylamine hydrochloride solution neutralized to pH 8.9 with 6 N sodium hydroxide. After stirring the mixture for 10 hours at 4°, the mixture was placed in a dialysis bag and dialyzed against two 500 ml portions of Tris-HCl buffer (0.05 M, pH 7.8) for one day. The volume of the protein mixture was then concentrated to 25 ml with Aquacide II (available from Calbiochem) and twice subjected to gel filtration chromatography, using each time, freshly packed Sephadex G-15, initially swollen in Tris-HCl buffer, 0.1 M, pH 9.0. The column size was 2.6×22.2 cm, the flow rate was 48 drops per minute, 40 drop fractions were collected, and the buffer of elution was Tris-HCl, 0.1 M, pH 9.0. The protein fractions were pooled and dialyzed against deionized water (5×2,000 ml portions) for 3 days. The conjugate solution was then lyophilized to yield 0.15 g of a white fluffy solid which was dried in vacuo over $P_2O_5$ for 3 days to yield 0.140 g of conjugate. Ultraviolet analysis indicated that 22 haptens were bound to each molecule of BSA.

EXAMPLE III

Carboxymethoxyacetyl Thyroxine Methyl Ester (DGMA)

To a solution of 1.65 g of the methyl ester of thyroxine hydrochloride in 80 ml of dry THF and 30 ml of chloroform in a flask protected from light was injected 300 μl of triethylamine while the mixture was agitated. Diglycolic anhydride (255 mg, 0.0022 mole) was then added and the mixture stirred overnight. The solution was then washed 3 times with water, dried over sodium sulphate and the volatiles removed in vacuo. The residue was purified on a 30 g Sephadex LH-20 column, using a solution of 20% methanol in dichloromethane as eluent. The clear fractions were collected, the solvent removed and the residue precipitated from methanol with water, yielding 1.53 g, 84 percent.

EXAMPLE IV

DGMA Conjugate to Bovine Serum Albumin

To a solution of 100 mg BSA in 30 ml aqueous 8 M urea at 0° was added slowly 25 ml of DMF, followed by the dropwise addition to 453 mg ($5.9 \times 10^{-4}$ mole) DGMA in 5 ml DMF. At completion of the addition, the pH of the reaction mixture was adjusted to 4.5 and 100 mg (0.0005 m) of ECDI hydrochloride was added in 10 mg portions at half-hour intervals to the stirring solution maintained at 0°. At the end of 5 hours, the reaction mixture was adjusted to pH 9 and dialyzed against 2 liters of 10% DMF in 4 M urea, pH 9. The precipitate was spun down and the supernatant dialyzed in a Dow Beaker Dialyzer against 25 gallons of 0.05 M carbonate, pH 9, followed by 5 gallons of ammonia water, pH 9. Lyophilization afforded 95 mg of conjugate which was shown by UV analysis to have 23 DGMA groups per BSA molecule.

EXAMPLE V

Methyl Methoxycarbimidomethoxyacetyl Thyroxinate Conjugate to BSA

A. To a suspension of 125 mg (1.1 mole) cyanomethoxyacetic acid in 1 ml dichloromethane was added 98 µl oxalyl chloride (146 mg, 1.15 mmole). One drop of dimethylformamide was added to initiate the reaction and the reaction mixture was stirred for 30 minutes until cessation of the effervescence and dissolution of the acid starting material. The solvent was then stripped off on the Rotavap and the remaining yellow oil added to a suspension of 827 mg (1 mmole) methylthyroxinate hydrochloride in 10 ml dry tetrahydrofuran containing 280 µl triethylamine (2 mmole). The reaction was ended after 2 hours when analytical thin-layer chromatography (silica gel, 25% ethyl ether in chloroform) showed no remaining thyroxine ester starting material. The reaction mixture was poured into water overlaid with ethyl acetate and the aqueous layer extracted three times with 50 ml of ethyl acetate. The organic layers were combined, washed once with water, once with brine, dried over magnesium sulfate and evaporated in vacuo to yield 888 mg (quantitative) of a pale yellow foam. Chromatography on Sephadex LH-20 (25 g, 10% methanol in ethyl acetate) provided removal of a polar impurity. Yield, 85 percent.

B. A solution of 89 mg of methyl cyanomethoxyacetyl thyroxinate (0.1 mmole) in 1 ml of dry methanol was placed in a dried, nitrogen-purged flask equipped with a serum stopper. A solution of sodium methoxide in methanol was added (1.1 equivalents of base) and the reaction stirred overnight in the dark. After 20 hours, thin-layer chromatography (25% ethyl ether in dichloromethane, silica gel) showed essentially complete reaction with some colored impurities.

C. A solution of the above imidate (0.1 mmole) in 2 ml of basic methanol (the untreated imidate formation reaction mixture) was added dropwise to a solution of 112 mg bovine serum albumin (~0.1 mmole lysine) in 5 ml of 0.05 M Tris buffer at pH 8.5. The pH of the reaction mixture was adjusted to pH 9.5 with 0.05 M hydrochloric acid and the reaction mixture stirred in the cold for 24 hours. The mixture was dialyzed against 10 l of dilute sodium bicarbonate solution and 3 l of deionized water. Analysis by ultraviolet spectroscopy indicated a conjugation number of approximately 20, based on an experimentally determined extinction coefficient for thyroxine of $6.2 \times 10^3 M^{-1} cm^{-1}$. Sephedex G-15 gel filtration (0.05 M Tris, pH 9 eluent) produced no change in the conjugation number.

EXAMPLE VI

(N-Carboxymethyl 3-Aza-3-methylglutaramic Acid Amide of Methyl Thyroxinate) Conjugate to MDH A. To a stirred solution of 0.201 g (0.22 mmole) T$_4$-MEMIDA, 1 ml dry THF, 25 mg (0.22 mmole) N-hydroxy succinimide and 30 µl dry triethylamine at 0° was added 0.048 g(0.25 mmole) of ECDI. The mixture was stirred for 35 minutes at 0°, then for 14 hours at 4°.

To 0.033 g (0.44 mmole) of glycine in 1.5 ml deionized water and 0.5 ml pyridine adjusted to pH 9 with 1 N NaOH at 0° was added dropwise the above solution with vigorous stirring. After continued stirring at 4° for 36 hours in the dark, the solvent was removed in vacuo and the residue dissolved in 5 ml abs. ethanol, and the ethanol evaporated, the ethanol treatment being repeated three times to yield a white foamy solid.

The residue was dissolved in 10 ml methanol, which was poured into 15 ml deionized water and extracted with 3 portions 25 ml each of ethyl acetate. The ethyl acetate layers were combined, extracted with 25 ml saturated brine and then dried over MgSO$_4$.

Volatiles were removed in vacuo, the residue dissolved in 2 ml methanol and chromatographed on silica gel (Et$_3$N:CH$_3$OH:CH$_2$Cl$_2$-2.1:10:90). The product was deadsorbed with CH$_3$OH/CH$_2$Cl$_2$, 1:1, the mixture filtered, the volatiles evaporated, and the residue dissolved in 5 ml THF and filtered again. After removal of volatiles, the residue was taken up in THF recrystallized from THF/HCCl$_3$/cyclohexane to yield 0.046 g, 21.6%.

B. Into a 1 ml vessel was charged 4.9 mg radioactive C$^{14}$ N-carboxymethyl 3-aza-3-methylglutaramic acid amide of methyl thyroxinate, dissolved in 39 µl DMF and cooled to 4°. To the DMF solution with stirring was added 51 µl of a 0.11 M ECDI solution in DMF at 4° and 10 µl of 0.5 M N-hydroxy succinimide in DMF at 4° and the mixture stirred overnight in the dark.

C. Pig heart mitochondrial MDH was dialysed against 0.05 M carbonate buffer, pH 9.0, to yield 4 ml of a $1.31 \times 10^{-5}$ M solution of MDH. To the solution was added 445 µl of DMF at 15 µl/min. The ester prepared above was added in 2 µl aliquots and enzyme activity assayed after an interval of 5 minutes. In a first reaction 5 µl of the ester was employed, while in a second reaction 9 µl was added for a ratio of thyroxine to MDH of 4.1 and 7.4 respectively.

Both reaction mixtures were dialysed three times against 300 ml 1 M K$_2$HPO$_4$, pH 9.8, once against 300 ml 0.05 M carbonate buffer (pH 9.0) and then two times against the phosphate buffer. The two reaction mixtures were then chromatographed at 4° on a Sephadex G-50 M column (0.9 × 54 cm) equilibrated with the phosphate buffer and eluted with the same phosphate buffer at a flow rate of 4 drops/min. and collected as 20 drop fractions. Active fractions were combined, the volume adjusted to 5 ml with the phosphate buffer and a 0.5 ml aliquot dialysed against 50 ml aliquot deionized water at 4°. The radioactivity of an aliquot was determined and assuming no protein loss, the number of haptens per protein molecule was 2.0 and 3.0.

EXAMPLE VII

T4-MEMIDA Conjugate to Malate Dehydrogenase

Into 250 μl of dry DMF was dissolved 10 mg (11 μmole) of T4-MEMIDA and 1.3 mg of N-hydroxysuccinimide. The reaction mixture was kept at 0° under a nitrogen blanket with stirring and 2.3 mg ECDI was added and the mixture maintained at 0° until the ECDI had dissolved. The solution was allowed to stand at 4° overnight.

A generalized procedure for preparing the conjugate is provided, with greater or lesser hapten numbers, depending upon the amount of the T4-MEMIDA hydroxysuccinimide ester employed in relation to the MDH. To 4 ml of a stirring solution of MDH (pig heart, mitochondrial, Miles, 5.0 mg/ml) in carbonate buffer, pH 9.2, was added one ml DMF. Successive additions of the T4-MEMIDA ester were made at about 60 to 90 minute intervals and aliquots withdrawn and assayed for enzyme activity. The following table indicates the order of addition, the amount of the addition, the time of the addition, the ratio of added T4 to MDH, and the percent deactivation observed. For conjugate number determinations, 2 to 20 μl of the conjugation mixture was added to 0.5 ml 1 M potassium monoacid phosphate at 0°. For enzyme activity determinations, 2 to 20 μl aliquots of the diluted conjugate was diluted to 0.8 ml with 0.1 percent rabbit serum albumin in glycine buffer, 0.1 M, pH 9.5, to which was added 100 μl of 0.108 M NAD and 100 μl of 2 M, pH 9.5 sodium malate. The rates were measured between 60 and 120 seconds after introduction at 30° in a Gilford Model 300-N spectrophotometer.

TABLE I

| Time | Addition T4-ester μl | Total[1] Volume μl | T4/MDH | T4[2] Conj. | % Deactivation |
|---|---|---|---|---|---|
| | | 4996 | 0/1 | | 0 |
| 10:34 | 13 | 5007 | 2/1 | | |
| 11:24 | | 5003 | 2/1 | | 30.1 |
| | 1 ml withdrawn as conjugate c | | | 1.3 | |
| 11:30 | 10.5 | 4011 | 4/1 | | |
| 12:03 | | 4009 | 4/1 | | 85.7 |
| | 1 ml withdrawn as conjugate d | | | 2.8 | |
| 1:10 | 8 | 3001 | 6/1 | | |
| 1:37 | | 2991 | 6/1 | | 94.0 |
| | 1 ml withdrawn as conjugate e | | | 3.7 | |
| 1:58 | 5.5 | 1977 | 8.1/1 | | |
| 2:49 | 4 | 1941 | 9.6/1 | | 98.8 |
| | 1 ml withdrawn as conjugate f | | | 5.6 | |

[1] samples were periodically withdrawn and the enzyme activity determined which were not reported, which affect the total volume reported
[2] No. of T4's bound to MDH

EXAMPLE VIII

T4-MEMIDA Conjugate to Triose Phosphate Isomerase (TIM)

Into 500 μl of dry DMF in a vial was introduced 6.0 mg (6.8 μmoles) T4-MEMIDA and 0.8 mg (7.3 μmoles) N-hydroxy succinimide, the vial flushed with dry argon and covered, and the mixture cooled in an ice bath. To the stirred mixture was then added 1.5 mg ECDI, the vial flushed with dry argon and stirred until everything dissolved. The vial was wiped dry, placed in covered plastic cup with Drierite ®, wrapped in foil and allowed to stand overnight at 4° with stirring.

To 1 ml triose phosphate isomerase (2 mg) in aqueous carbonate buffer (0.1 M, pH 9.2) at 4°, 0.3 ml DMF was added slowly with syringe. The ester solution was added slowly in increments by syringe and the enzyme activity monotored. When the enzyme was approximately 72% deactivated, DMF was added to bring the solution to 40% volume DMF.

The cold reaction mixture was passed through a Sephadex ® G-25-(medium) column equilibrated with 0.1 M carbonate buffer, pH 9.2. The column was a 50 cc buret, 1.1 cm in diameter with a bed volume of ~19 ml. The elution was carried out at 4° with a solution of 60 parts by volume of an aqueous solution 0.1 M $CO_3$, pH 9.2 and 0.3 M ammonium sulfate and 40 parts of DMF. Fractions were collected varying in volume from about 1 to 4 ml. Fractions 5 and 6 were pooled (2.4 ml) and dialysed first against ~100 ml aqueous 20 volume % DMF, 0.02 M triethanolamine (TEA), pH 7.9, then 3×250 ml aqueous 0.02 TEA, pH 7.9. The ratio of conjugated T-4 to enzyme was about 6.

EXAMPLE IX

Desaminothyroxine conjugate to MDH

Desaminothyroxine (9.1×10hu −3 g, $1.2 \times 10^{-5}$ mole) $1.4 \times 10^{-3}$ g ($1.2 \times 10^{-5}$ mole) of NHS, and 0.25 ml of dry DMF were successively added to a 1 ml reaction vessel. The reaction mixture was cooled in an ice bath and $2.5 \times 10^{-3}$ g ($1.3 \times 10^{-5}$ mole) of ECDI added under a $N_2$ blanket. The reaction mixture was stirred overnight at 4°.

With cooling on an ice bath, and with stirring, DMF (0.23 ml) was slowly to $1.9 \times 10^{-3}$ g ($2.8 \times 10^{-8}$ mole) of MDH in 0.83 ml of 0.05 M $NaNCO_3$—$Na_2CO_3$ (pH 9.0) with stirring while cooled in an ice bath. The above ester solution (5.8 μl) was then added, with stirring and the stirring continued for one hour while maintaining the temperature. The conjugation mixture was gel filtered on three 0.9×13 cm Sephadex ® G-50 M columns to yield a desaminothyroxine/MDH conjugate which was 91% deactivated and which had a hapten number of 2.5 (by iodine analysis). The conjugate enzyme acitivity was found to be 30% activated when treated with anti-T4 sera.

EXAMPLE X

T4-MEMIDA Glycine

A 3 ml Pierce Reacti-Vial™ was charged with 0.201 g ($2.18 \times 10^{-4}$ mole) of T4-MEMIDA and 0.025 g ($2.17 \times 10^{-4}$ mole) of N-hydroxysuccinimide (NHS). Two ml of dry THF and 30 μl ($2.15 \times 10^{-4}$ mole) of dry triethylamine were added and the reaction mixture was cooled to 0° with an ice bath. ECDI (0.048 g, $2.50 \times 10^{-4}$ mole) was added as a powder and the reaction mixture stirred for 35 minutes at 0°. The reaction mixture was then placed in the cold room (2°) and stirred for 15 hours. A TLC of the reaction mixture after 15 hours showed two spots with $R_1$ values of 0.06 (T4-MEMIDA) and 0.60 (T4-MEMIDA NHS ester), on an analytical silica gel plate, with 10% methanol in dichloromethane as the irrigant. A 25 ml flask, equipped with stirring flea and septum stopper, was charged with 0.033 g ($4.39 \times 10^{-4}$ mole) of glycine, followed by 1.50 ml of distilled $H_2O$, 0.50 ml of pyridine, and 100 μl ($1.00 \times 10^{-4}$ mole) of 1.0 N NaOH. The reaction mixture was cooled to 0° with an ice bath. With vigorous stirring, the T4-MEMIDA NHS ester solution, prepared above, was added dropwise, and after addition the reaction mixture was placed in the cold room (2°) and stirred for 36 hours. The solvents were then stripped with a rotary evaporator to yield an oily pyridine-smelling solid. This solid was taken up in 10 ml MeOH and poured into 15 ml H$_2$O and the solution was extracted with ethyl acetate (2×25 ml). The combined organic layers were extracted once with 25 ml of saturated brine, then dried over anhydrous MgSO$_4$. After filtration, the ethyl acetate was stripped on a rotary evaporator to yield a white crystalline solid. The solid was taken up in 2 ml of methanol and put onto four preparative silica gel plates TLC plates, which were developed in triethylamine:methanol:dichloromethane (2.1:10:90). The plates were run twice, then were scraped and the product deabsorbed with methanol:dichloromethane (1:1). The silica gel was filtered off and the filtrate reduced to 2 ml in vacuo. A TLC of the product in THF showed only one spot with a R$_f$ value of 0.50, on an analytical silica gel TLC plate, in triethylamine:methanol:dichloromethane (2.1:10:90). The product was recrystallized from THF/chloroform/cyclohexane.

EXAMPLE XI

T$_4$-MEMIDA Glycylglycine

A 3 ml Pierce Reacti-Vial ™ was charged with 0.202 g (2.20×10$^{-4}$ mole) of T$_4$-MEMIDA, and 0.025 g (2.17×10$^{-4}$ mole) of NHS. Dry THF (2 ml) and 31 µl of dry triethylamine were added, and the reaction mixture was cooled to 0°. ECDI (0.051 g, 2.66×10$^{-4}$ mole) was added and the reaction mixture stirred in the cold room (2°) for 8.25 hours. A TLC indicated the formation of the T$_4$-MEMIDA NHS ester; R$_f$ value of 0.63, on an analytical silica gel plate, with triethylamine:methanol:dichloromethane (2.1:10:90). A 25 ml flask, equipped with stirring flea and septum stopper, was charged with 0.058 g (4.39×10$^{-4}$ mole) of glycylglycine, followed by 1.50 ml of H$_2$O and 0.50 ml of pyridine and 100 µl (1.0×10$^{-4}$ mole) of 1.0 N NaOH. The reaction mixture was cooled to 0°, and the T$_4$-MEMIDA NHS ester solution added dropwise with stirring. After addition of the activated ester, 1.0 ml deionized H$_2$O and 0.50 ml of pyridine was added. The reaction mixture was stirred in the cold room (2°) for 93 hours, worked up identical to that of T$_4$-MEMIDA glycine to yield 0.018 g (9% yield) of a tan gold solid. The product was homogeneous by TLC on silica gel with triethylamine:methanol:dichloromethane (2.1:10:80); R$_f$ value of 0.81, where the plate was developed twice.

EXAMPLE XII

T$_4$-MEMIDA Glycine/MDH Conjugate

A 1 ml Pierce Reacti-Vial ™, equipped with stirring flea, was charged with 0.049 g (5.0×10$^{-6}$ mole) of T$_4$-MEMIDA and 39 µl of dry DMF. The reaction mixture was cooled to 0° and 10 µl (5.2×10$^{-6}$ mole) of a 5.0×10$^{-1}$ M NHS in DMF at 0° solution and 51 µl (6.1×10$^{-6}$ mole) of a 1.2×10$^{-1}$ M ECDI in DMF solution at 0° were added and the reaction mixture stirred in the cold room (2°) for 49 hours. A TLC of the reaction mixture, after 49 hours, showed two spots with R$_f$ values of 0.49 (T$_4$-MEMIDA glycine) and of 0.68 (T$_4$-MEMIDA glycine NHS ester), on analytical silica gel plates, developed in triethylamine:methanol:dichloromethane (2.1:10:90). MDH (4.0 ml, 1.3×10$^{-5}$ M, 0.05 M NaHCO$_3$—Na$_2$CO$_3$, pH 9.2), was put into a 10 ml round bottomed flask equipped with stirring bar and septum stopper, cooled to 0°, and the enzyme activity was determined, as described previously. Dry DMF (445 µl) was added to the reaction mixture at a rate of 15 µl per minute to yield a 10% DMF reaction mixture. The enzyme activity was again determined. The 4.3×10$^{-2}$ M T$_4$-MEMIDA glycine NHS ester solution was added to the reaction mixture in 1 to 2 µl aliquots, and the enzyme activity was determined after each addition. Nine microliters of the above activated ester solution gave an 82% deactivated enzyme conjugate. After the final addition of activated ester, the enzyme reaction mixture was exhaustively dialyzed against 1.0 M K$_2$HPO$_4$ (with 1.0×10$^{-3}$ M NaN$_3$), at 2°. After dialysis, the enzyme conjugate was carefully removed from the dialysis bag and was passed through two Sephadex ® G-50 M (preswollen in 1.0 M K$_2$HPO$_4$, with 1.0×10$^{-3}$ M NaN$_3$) columns. The two column sizes were 0.9×54.0 cm and 0.9×51.0 cm, the flow rates were 4 to 5 drops per minute, and 20 drop fractions were collected. The protein fractions were concentrated using a collodion bag apparatus, in the cold room. The hapten number was determined to be 3.0.

EXAMPLE XIII

T$_4$-MEMIDA glycylglycine/MDH Conjugate

ECDI (0.015 g, 7.8×10$^{-5}$ mole) was dissolved in 0.50 ml of dry DMF to yield a 1.6×10$^{-1}$ M solution. NHS (0.75 g, 6.5×10$^{-4}$ mole) was dissolved in 1.0 ml of dry DMF to yield a 6.5×10$^{-1}$ M solution. Both solutions were cooled to 0°, in an ice bath, prior to use. A 1 ml Pierce Reacti-Vial ™, equipped with stirring flea, was chaged with 2.4×10$^{-3}$ g of T$_4$-MEMIDA glycylglycine, followed by 78 µl of ice cold dry DMF, cooled in an ice bath, and then 4 µl of a 6.5×10$^{-1}$ M NHS in DMF solution at 0° and 18 µl of a 1.6×10$^{-1}$ M ECDI in DMF solution at 0° were added.

The reaction mixture was placed in the cold room (2°) and stirred for 20 hours. At the end of this time, a TLC of the reaction mixture showed two spots with R$_f$ values of 0.25 (T$_4$-MEMIDA glycylgylcine) and of 0.59 (T$_4$-MEMIDA glycylglycine NHS ester), on analytical silica gel plates, developed in triethylamine:methanol:dichloromethane (2.1:10:90. MDH (4.0 ml of a 1.5×10$^{-5}$ M, 0.05 M NaHCO$_3$—Na$_2$CO$_3$ (pH 9.2)), was put into a 10 ml round bottomed flask, equipped with stirring bar and septum stopper. The reaction mixture was cooled to 0°, with an ice bath, and 440 µl of dry DMF was added at a rate of 50 µl per minute. The enzyme activity was determined before and after the DMF addition. The 1.9×10$^{-2}$ M T$_4$-MEMIDA glycylglycine NHS ester solution was added to the reaction mixture in 3 to 10 µl aliquots and the enzyme activity was determined after each addition. The addition of 29 µl of the activated ester solution gave an 82% deactivated enzyme conjugate. The reaction mixture was then exhaustively dialyzed against 1.0 M K$_2$HPO$_4$ (with 1.0×10$^{-3}$ M NaN$_3$), at 2°. After dialysis, the conjugate was passed through three Sephadex ® G-50 M columns (preswollen in 1.0 M K$_2$HPO$_4$ with 1.0×10$^{-3}$ M NaN$_3$) and was eluted with the same buffer. The column sizes were 0.9×55 cm, 0.9×56 cm, and 0.9×56 cm, the flow rates were 4 to 5 drops per minute, and 20 drop fractions were collected. The protein fractions were concentrated using a collodion bag apparatus, in the cold room. The hapten number was determined to 3.9, by the method previously described.

Antibodies were prepared employing the antigen conjugates. Initially 2 mg of the conjugate was injected. Then 0.25 mg of the conjugate was injected at two week intervals. With sheep, the individual injection was a total of 2 ml, of which 0.5 ml was the conjugate dissolved in saline plus 1.5 ml of Freund's complete adjuvant. 0.25 ml aliquots were injected subcutaneously into each of 4 sites and 0.5 ml aliquots were injected intramuscularly into each hind leg.

With rabbits, the total injection was 0.75 ml, with 0.25 mg of the conjugate dissolved in 0.25 ml saline, and 0.5 ml of Freund's complete adjuvant added. Injections of 0.09 ml were injected subcutaneously into 4 sites and injections of 0.19 ml injected into each hind leg.

The animals are normally bled about 5 to 7 days after each injection and the antibodies isolated according to conventional procedures.

To demonstrate the utility of the thyroxine-MDH conjugate for assaying for $T_4$, a number of assays were carried out. In a first series of assays, the assays were carried out with varying amounts of antibody to demonstrate the increase in activity of the enzyme conjugate with increasing amounts of antibody. In a second series of assays, varying amounts of $T_4$ were added to antibody, so as to change the effective concentration of antibody which is available for binding to the MDH-bound-thyroxine. From these results it is shown, that by establishing a standard curve based on samples containing known amounts of thyroxine, one can determine the amount of thyroxine which is free in serum by relating the observed values of the enzyme activity to the standard curve.

The assay procedure is as follows. A 0.8 ml solution of 0.1 weight percent RSA in 0.1 M glycinate buffer, pH 9.5, containing $10^{-3}$ M EDTA, is prepared of the antibody solution, and the MDH-bound-T-4. The solution is incubated for 45 minutes, at which time the substrates (100 µl 2 M malate and 100 µl 0.108 M NAD) are added and the solution is transferred to a spectrophotometer and the values read at 30°, as the change in optical density between 120 seconds and 60 seconds from the introduction into the spectrophotometer. For the conjugates prepared in Example VII, employing sheep antibody, the following table indicates the results.

TABLE II

| | conjugate Example VII | | | |
|---|---|---|---|---|
| $Ab_{T-4}$[1] µl | $c^2$ % change | $d^2$ % change | $e^2$ % change | $f^2$ % change |
| 0 | — | — | — | — |
| 1 | +17 | 113 | 246 | 34 |
| 2 | +17 | 124 | 358 | 111 |
| 3 | +17 | 130 | 389 | 190 |
| 4 | +17 | 126 | 399 | 290 |
| 5 | +17 | 129 | 427 | 376 |
| 10 | +17 | 130 | 467 | 665 |
| 15 | +17 | 136 | 471 | 725 |
| 20 | +17 | 139 | 503 | 829 |
| 25 | +17 | 144 | 485 | 825 |

[1] ~$9.0 \times 10^{-6}$ M $Ab_{T-4}$ based on binding sites; K = $1.12 \times 10^=$
[2] Concentration (M) of enzyme
c - $5 \times 10^{-10}$
d - $2.56 \times 10^{-9}$
e - $1.4 \times 10^{-8}$
f - $3.7 \times 10^{-8}$ A series of assays were now carried out, whereby a thyroxine solution of 9.7 mg in 25 ml of 0.05 N sodium hydroxide was serially diluted with 0.05 N sodium hydroxide. The assays were carried out by combining 600 µl of 0.1% rabbit serum albumin, 100 µl of antibody in 0.1 M glycine buffer, pH 9.5, $10^{-3}$ M EDTA and 100 µl of the $T_4$ solution and the mixture incubated for 15 minutes at room temperature. To the solution was then added a specified volume of the MDH-bound-T-4 solution and the mixture incubated for 10 minutes. The substrates were then added and readings were taken in a spectrophotometer at 30° as indicated previously. The following table indicates the results.

TABLE III[3]

| $T_4$ Sample conc, M | Conjugate[1,2] | | |
|---|---|---|---|
| | c ΔOD | d ΔOD | e ΔOD |
| — | 91 | 81 | 248 |
| $5 \times 10^{-10}$ | 89 | 83 | 254 |
| $5 \times 10^{-9}$ | 88 | 82 | 255 |
| $5 \times 10^{-8}$ | 90 | 81 | 249 |
| $5 \times 10^{-7}$ | 88 | 77 | 212 |
| $5 \times 10^{-6}$ | 95 | 54 | 93 |
| $5 \times 10^{-5}$ | 99 | 56 | 85 |

[1] volume of enzyme conjugate employed and concentration
c - 15µl $1.11 \times 10^{-7}$ M
d - 5µl $5.12 \times 10^{-7}$ M
e - 5µl $2.81 \times 10^{-6}$ M
[2] anti-thyroxine $9 \times 10^{-6}$ M in binding sites diluted 1 to 33 prior to addition in 100µl
[3] ΔOD × $10^3$ Following the procedure described in Example VII, another conjugate was prepared which was chromatographed on a Sephadex G-50 column which had been equilibrated with 1 M potassium monoacid phosphate. The flow was slow and 20 drop fractions were collected until tube 39, after which time 99 drop fractions were collected. The process was repeated with a second G-50 column, each time concentrating the collected fractions with Sephadex G-200 by ultrafiltration. By analysis, the number of T-4 groups per enzyme was determined to be from 4.3 to 5.3, average 4.8.

A series of assays were carried out using various sources of anti-serum and varying concentrations of thyroxine. As described in the previous procedure, the antibody and thyroxine were combined with a 0.1 percent glycine buffered RSA solution and incubated 15 minutes, followed by the addition of the indicated amount of enzyme solution, the assay mixture incubated for an additional 10 minutes, the substrates added, and then introduced into a spectrophotometer, the second minute being read as to the change in optical density units. The volume of antibody added is one µl and the volume of enzyme added is one µl. The following table indicates the results.

TABLE IV[1]

| $T_4$ Assay conc. M | Antisera | | |
|---|---|---|---|
| | A ΔOD | B ΔOD | C ΔOD |
| — | 76 | 61 | 87 |
| $5 \times 10^{-5}$ | 20 | 24 | 26 |
| $5 \times 10^{-6}$ | 28 | 29 | 29 |
| $5 \times 10^{-7}$ | 30 | 39 | 32 |
| $5 \times 10^{-8}$ | 38 | 50 | 62 |
| $5 \times 10^{-9}$ | 73 | 59 | 84 |
| $5 \times 10^{-10}$ | 81 | 61 | 94 |
| $5 \times 10^{-11}$ | 78 | 63 | 92 |

[1] ΔOD × $10^3$

In carrying out the T-4 Assay employing TIM-T-4 conjugate, the following reagents were employed.

TIM-T-4 Assay Reagents

Buffer:
0.02 M triethanolamine (TEA)-HCl, pH, 7.9;
0.0054 M ethylene diamine tetraacetic acid (EDTA).

Rabbit serum albumin solution: 0.2 wt. % RSA, in buffer.

TIM-T-4 solution: $\sim 7 \times 10^{-3}$ $\mu$M of T-4, as TIM-T-4, in RSA solution (provides assay rate of $\sim 200$ OD/min)

Anti-T-4 solution: $\sim 4 \times 10^{-5}$M anti-T-4 based on binding sites in RSA solution.

NADH solution: 2.5 mg NADH/ml in buffer (stock solution) prepared according to TEKIT instructions and diluted 1:7 parts by weight with buffer).

DL-glyceraldehyde-3-phosphate solution (GAP): Prepared from DL-glyceraldehyde-3-phosphate diethylacetal, Ba salt from Sigma Chemical Co., St. Louis, Mo., 1.5 g of salt treated to give final volume of 10 ml.

α-glycerophosphate dehydrogenase (α-GPDH) solution: 0.2 mg/ml in buffer (Boehringer-Mannheim).

Thyroxine (T-4 solution): $2.57 \times 10^{-4}$ M in RSA solution.

The assay was carried out as follows. A number of dilutions of the T-4 solution were prepared. Initially, 0.4 ml of the T-4 solution, 0.4 ml of the TIM-T-4 solution and 0.4 ml of the antibody solution was mixed, and set in a 30° water bath for 12 minutes. To the solution was then added 200 $\mu$l of the NADH solution, 25 $\mu$l of the alpha-GPDH solution and 100 $\mu$l of the GAP solution. The assay tube was covered with parafilm and an aliquot was then aspirated into a thermocuvette in a 300 N Gilford Spectrophotometer and the first reading made after 30 seconds while in the machine at 30° C. The optical density was read at 366 nm at 30° C. The remainder of the assay solution was maintained in a 30° C. bath and read after 13 minutes. The following table indicates the results.

TABLE V

| Sample No. | T-4 Soln. Conc. | Decrease in OD in 13' |
|---|---|---|
| 1 | 0 | 0.543 |
| 2 | $3.84 \times 10^{-6}$ | 0.550 |
| 3 | $7.68 \times 10^{-6}$ | 0.550 |
| 4 | $1.54 \times 10^{-5}$ | 0.490 |
| 5 | $6.14 \times 10^{-5}$ | 0.448 |
| 6 | $1.29 \times 10^{-4}$ | 0.422 |
| 7 | $5.14 \times 10^{-4}$ | 0.409 |

The results of the foregoing tables demonstrate that extremely low concentrations, as well as extremely small amounts of thyroxine can be detected by the subject method. The method is quite straightforward in requiring few manipulative steps. By combining the reagents in a buffered medium, and optionally incubating the mixture, followed by the addition of the enzyme substrates, one can determine T-4 by a spectrophotometric reading over a short period of time. The system allows for automation, so that samples and reagents can be mixed automatically and read.

Although the foregoing invention has been described in some detail by way of illustration and example for purposes of clarity of understanding, it will be obvious that certain changes and modifications may be practiced within the scope of the appended claims.

What is claimed is:

1. An ENZ-bound-ligand of the formula

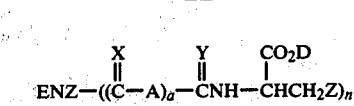

wherein:
ENZ is an enzyme reversibly inhibited by ligand selected from the group consisting of malate dehydrogenase and triose phosphate isomerase;
a is 0 or 1;
n is on the average at least one and not more than about 10;
X and Y are the same or different and are chalcogen or amino;
D is hydrogen or an alkyl group of from 1 to 6 carbon atoms;
Z is 3,5-diiodo-4-(3',5'-diiodo-4'-hydroxyphenoxy-1') phenyl-1; and
A is a bond or an organic divalent group of from 1 to 12 carbon atoms and 0 to 6 heteroatoms which are oxygen, sulfur or nitrogen, the total number of heterofunctionalities being in the range of 0 to 4.

2. An ENZ-bound-ligand according to claim 1 wherein ENZ is triose phosphate isomerase.

3. An ENZ-bound-ligand according to claim 1, wherein said dehydrogenase is malate enzyme.

4. An ENZ-bound-ligand according to claim 3, wherein n is 1 to 8, D is an alkyl group of from 1 to 3 carbon atoms, and A is an aliphatic organic divalent radical of from 1 to 10 carbon atoms having from 0 to 2 heteroatoms in the chain between the non-oxo-carbonyl groups which are oxygen and nitrogen and are present as oxy, tertiary amino or amido and having a total of 0 to 4 heteroatoms which are oxygen or nitrogen.

5. An ENZ-bound-ligand according to claim 1, wherein n is on the average of from 1 to 8, X and Y are chalcogen, D is an alkyl group of from 1 to 6 carbon atoms, and A is an aromatic group of from 6 to 8 carbon atoms having from 0 to 4 heteroatoms which are oxygen, nitrogen, and sulfur.

6. An MDH-bound-ligand reversibly inhibited by said ligand and of the formula

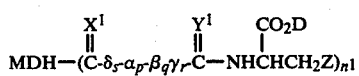

wherein:
MDH is malate dehydrogenase;
$n^1$ is on the average in the range of about 1 to 8;
$X^1$ and $Y^1$ are the same or different and are oxygen, sulfur or imino;
p, q and r are each 0 or 1;
s is 0 to 2;
α and γ are hydrocarbon groups of from 1 to 8 carbon atoms, β is oxy, thio, sufonyl or alkylamino, wherein the alkyl group is of from 1 to 3 carbon atoms, with the proviso that β is amino or alkylamino when p is 0;
δ is

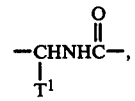

wherein $T^1$ is hydrogen or lower alkyl of from 1 to 3 carbon atoms;

Z is 3,5-diiodo-4-(3',5'-diiodo-4'-hydroxyphenoxy-1')phenyl-1; and

D is hydrogen or an alkyl group of from 1 to 6 carbon atoms.

7. An MDH-bound-ligand according to claim 6, wherein s is 0, beta is alkylamino, alpha and gamma are from 1 to 3 carbon atoms, p, q and r are all one.

8. An MDH-bound-ligand according to claim 6, wherein beta is oxy, alpha and gamma are from 1 to 3 carbon atoms, s is 0, and p, q and r are all one.

9. An MDH-bound-polyiodothyronine having from 1 to 10 thyroxine groups bound to said MDH.

10. An MDH-bound-polyidothyronine according to claim 9, having from 2 to 6 thyroxine groups bound to MDH.

11. An MDH-bound-thyroxine reversibly inhibited by said thyroxine having on the average from about 1 to 10 thyroxines of the formula $$\begin{array}{c} DO_2CCHCH_2Z \\ | \\ NH_2 \end{array}$$

bonded at the amino group to MDH by a non-oxo-carbonyl group including the nitrogen and sulfur analogs thereof;

wherein:
D is hydrogen or an alkyl group of from 1 to 6 carbon atoms; and
Z is 3,5-diiodo-4-(3',5'-diiodo-4'-hydroxyphenoxy-1')phenyl-1.

12. An MDH-bound-polyiodothyronine reversibly inhibited by said polyiodothyronine of the formula $$MDH-(COCH_2(CH_2)_tZ)_{n^1}$$

wherein;
t is 0 or 1;
$n^1$ is on the average in the range of 1 to 10;
MDH is malate dehydrogenase; and
Z is 3,5-diiodo-4-(3',5'-diiodo-4'-hydroxyphenoxy-1')phenyl-1.

13. A TIM-bound-polyiodothyronine reversibly inhibited by said polyiodothyronine of the formula $$TIM((\overset{X}{\overset{\|}{C}}-A)_a-\overset{Y}{\overset{\|}{C}}NH-\overset{CO_2D}{\overset{|}{C}}HCH_2Z)_n$$

wherein
TIM is triose phosphate isomerase;
a is 0 or 1;
n is on the average at least one and not more than about 10;
X and Y are the same or different and are chalcogen or imino;
D is hydrogen or an alkyl group of from 1 to 6 carbon atoms;
Z is 3,5-diiodo-4-(3',5'-diiodo-4'-hydroxyphenoxy-1')phenyl-1; and
A is a bond or an organic divalent group of from 1 to 12 carbon atoms and 0 to 6 heteroatoms which are oxygen, sulfur or nitrogen, the total number of heterofunctionalities being in the range of 0 to 4.

* * * * *